(12) United States Patent
Ludwig et al.

(10) Patent No.: US 12,156,681 B2
(45) Date of Patent: Dec. 3, 2024

(54) SET FOR DORSAL SPINAL FUSION AND HANDLE FOR A MEDICAL TOOL

(71) Applicant: Richard Wolf GmbH, Knittlingen (DE)

(72) Inventors: Volker Ludwig, Eltville (DE); Christian Röbling, Eltville (DE)

(73) Assignee: Richard Wolf GmbH, Knittlingen (DE)

( * ) Notice: Subject to any disclaimer, the term of this patent is extended or adjusted under 35 U.S.C. 154(b) by 548 days.

(21) Appl. No.: 17/605,360

(22) PCT Filed: Apr. 8, 2020

(86) PCT No.: PCT/EP2020/059960
§ 371 (c)(1),
(2) Date: Oct. 21, 2021

(87) PCT Pub. No.: WO2020/216616
PCT Pub. Date: Oct. 29, 2020

(65) Prior Publication Data
US 2022/0160406 A1 May 26, 2022

(30) Foreign Application Priority Data
Apr. 23, 2019 (DE) ...................... 10 2019 110 442.4

(51) Int. Cl.
| | | |
|---|---|---|
| *A61B 17/70* | (2006.01) | |
| *A61B 50/20* | (2016.01) | |
| *A61B 50/33* | (2016.01) | |
| *B25B 15/04* | (2006.01) | |
| *B25B 23/00* | (2006.01) | |
| *A61B 17/00* | (2006.01) | |
| *A61B 50/00* | (2016.01) | |
| *A61B 50/30* | (2016.01) | |

(52) U.S. Cl.
CPC ...... *A61B 17/7082* (2013.01); *A61B 17/7091* (2013.01); *A61B 50/20* (2016.02); *A61B 50/33* (2016.02); *A61B 2017/00407* (2013.01); *A61B 2017/0046* (2013.01); *A61B 2050/0065* (2016.02); *A61B 2050/3008* (2016.02)

(58) Field of Classification Search
CPC . A61B 17/7082; B25B 15/04; B25B 23/0035; B25B 23/0042
See application file for complete search history.

(56) References Cited

U.S. PATENT DOCUMENTS

| | | | | |
|---|---|---|---|---|
| 5,368,480 A | * | 11/1994 | Balfour ................ | A61C 8/0089 433/141 |
| 9,615,838 B2 | * | 4/2017 | Nino ................... | A61B 17/3496 |
| 9,919,412 B2 | * | 3/2018 | Petit ........................ | B25G 1/08 |

(Continued)

FOREIGN PATENT DOCUMENTS

| | | |
|---|---|---|
| DE | 202008009123 U1 | 9/2008 |
| DE | 202012100244 U1 | 5/2012 |
| WO | 2013178932 A1 | 12/2013 |

*Primary Examiner* — Nicholas W Woodall
(74) *Attorney, Agent, or Firm* — Smartpat PLC

(57) ABSTRACT

A set for dorsal spinal fusion comprises a detachable handle made of plastic material and a screwdriver that can be coupled to the removable handle without the use of tools. A receptacle of the handle for the screwdriver is made of plastic material. Also, a handle is disclosed, which in particular comprises a ratchet mechanism.

18 Claims, 12 Drawing Sheets

(56) References Cited

U.S. PATENT DOCUMENTS

| | | | |
|---|---|---|---|
| 2003/0188605 A1* | 10/2003 | Chang | B25B 15/04 |
| | | | 81/60 |
| 2006/0241627 A1* | 10/2006 | Reo | A61B 17/1671 |
| | | | 606/79 |
| 2012/0222524 A1* | 9/2012 | Floyd | B25B 23/0042 |
| | | | 81/60 |
| 2015/0174754 A1 | 6/2015 | Petit | |
| 2016/0214242 A1* | 7/2016 | Ivinson | B23B 31/1071 |
| 2016/0346017 A1 | 12/2016 | Meyer et al. | |
| 2017/0065322 A1 | 3/2017 | Prado et al. | |
| 2017/0189082 A1 | 7/2017 | Petit | |
| 2017/0224399 A1 | 8/2017 | Coillard-Lavirotte et al. | |
| 2019/0022833 A1 | 1/2019 | Macke et al. | |

* cited by examiner

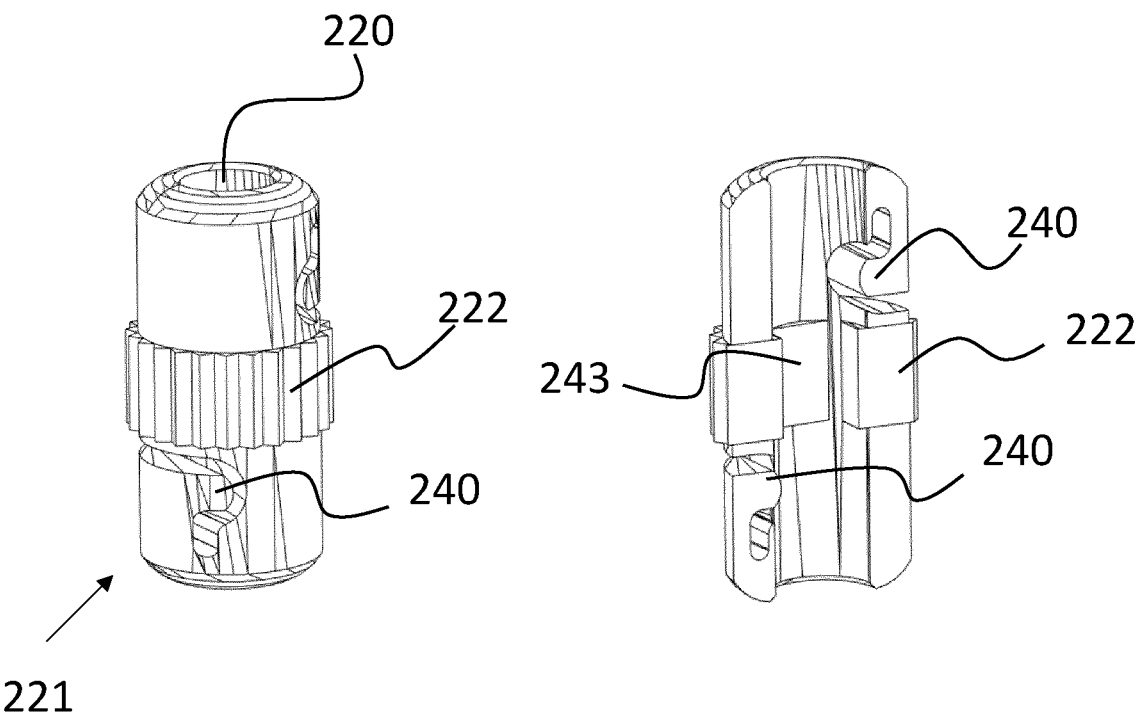
Fig. 10                                    Fig. 11
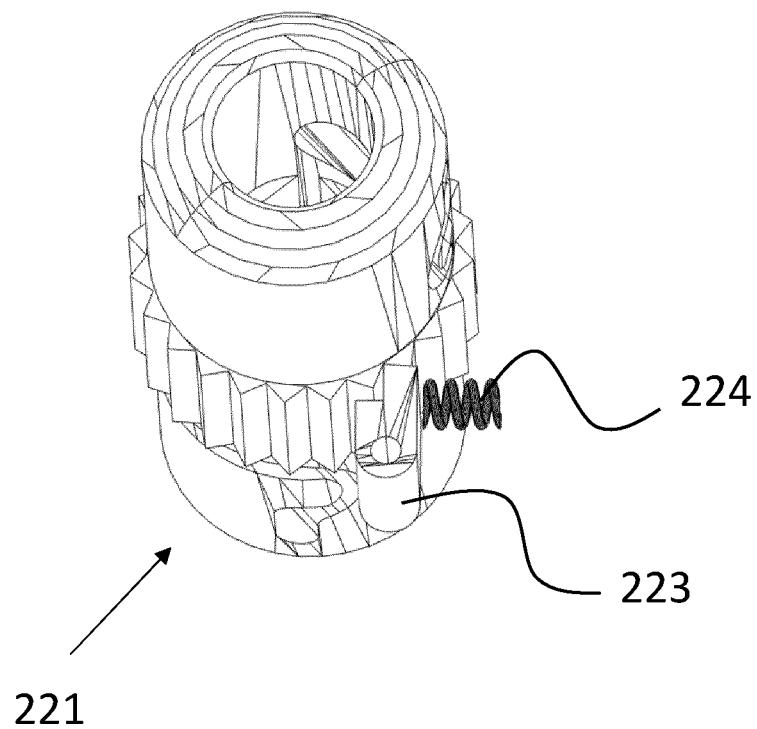
Fig. 12

SET FOR DORSAL SPINAL FUSION AND HANDLE FOR A MEDICAL TOOL

CROSS-REFERENCE TO RELATED APPLICATION

This application is a national stage application, filed under 35 U.S.C. § 371, of International Patent Application No. PCT/EP2020/059960, filed on 2020 Apr. 8, which claims the benefit of German Patent Application No. 10 2019 110 442.4, filed 2019 Apr. 23.

TECHNICAL FIELD

The disclosure relates to a set for dorsal spinal fusion and to a handle especially designed for this purpose, which is in particular designed for receiving a drive of a screwdriver.

BACKGROUND

In the practice of dorsal spinal fusion, screws are in particular used, which comprise a head having a tulip with a passage for a fusion rod.

The screws in the form of bone screws are introduced into the vertebral body, and then a rod is inserted through the opening in the tulips of the screw heads. Once the rod has been fastened by a lock, the vertebral bodies will be blocked through the rods.

For this purpose, an extensive range of instruments is usually used in practice. Usually, an access needle is first used to puncture through the skin to mark the canal.

Then, a guide wire is introduced, a dilator is used to expand the soft tissue, and the screws are introduced which are then coupled to the rods.

Finally, the rods can each be fixed with a lock. This may in particular be a lock comprising a nut with a breakaway head piece which breaks off when a design-specific predetermined torque is reached.

Detachable handles can be used as a drive, especially for the screwdrivers that are used. What has been established in practice is in particular a square drive on the screwdrivers, which can be locked to a handle without the use of tools.

Since the introduction of the screws is cumbersome, some users prefer ratchet handles. Such a ratchet handle is known from document WO 2013/178932 A1, for example.

The sets known from practice, which include at least some of the instruments required for dorsal spinal fusion, are mostly designed entirely as reusable instruments. This inevitably entrains a costly and laborious sterilization of the instruments after each use.

However, in the instruments known from practice, in particular those comprising the aforementioned ratchet handle, the receptacle for the drive of the tool usually has such a complex configuration that the handles are very expensive to manufacture.

Therefore, it makes no sense to use a handle of this type, which in particular includes a sleeve made of metal as a receptacle for the drive as part of a single-use instrument set.

SUMMARY

By contrast, an object of the disclosure is to provide a set for dorsal spinal fusion and a handle that can be used for this purpose, which are simple and cost-efficient to manufacture and which in particular allow to provide a disposable, i.e. single-use instrument set.

The object of the invention is achieved by a set for dorsal spinal fusion and by a handle for a medical tool according to any one of the independent claims.

Preferred embodiments and refinements of the invention will be apparent from the subject-matter of the dependent claims, the description, and the drawings.

The disclosure relates to a set for dorsal spinal fusion, which in particular comes in the form of a disposable, i.e. single-use set of instruments. The tools included in the set can in particular be provided in sterile packaging, for example in a tear-open blister pack.

The set comprises at least one detachable handle made of plastics material and at least one screwdriver that can be coupled to the detachable handle without the use of tools, and a receptacle of the handle for the screwdriver is made of plastics material.

In contrast to prior art handles having a receptacle which commonly comprises a metal sleeve overmolded with plastics material, the disclosure makes it possible to form the receptacle for the tool drive integrally with the handle.

It has been found that a suitable handle can be produced in this way at low cost.

In particular when choosing a suitable plastics material, a receptacle made of plastics material will be sufficient for use of the handle in combination with a single-use instrument set.

Therefore, in particular the receptacle for the drive of the screwdriver is made of plastics material. It may, for example, be polygonal, in particular it may have a square shape.

The handle is preferably made of a polymer, in particular a thermoplastic material. This allows it to be produced by injection molding.

A polyacrylamide has proven to be particularly suitable.

In particular a fiber-reinforced plastics material can be used for the handle, specifically a glass fiber-reinforced polyacrylamide.

According to a preferred embodiment, the handle comprises a tool receptacle made of plastics material, and the drive of a tool can be locked therein by means of a resilient hook made of plastics material, which is an integral part of the handle.

So, for locking the tool in place, a resilient hook is used, for example an L-shaped hook which can be formed integrally with the main body of the handle or with a portion of the handle.

The hook is resilient by virtue of the resilient properties of the plastics material. Thus, there is no need for a separate spring.

The resilient hook may in particular be an integral part of a main body of the handle or an integral part of the sleeve of a ratchet mechanism.

The handle is preferably in the form of an elongated handle.

According to one embodiment, a tool receptacle is provided on both the long side and the narrow end thereof.

Therefore, depending on the intended use and preference, the handle can be used so as to form a T-shaped assembly with the tool, or, when coupled to the narrow end thereof, so as to be aligned axially to the tool according to the main extension direction thereof.

The T-shaped assembly enables to apply the highest possible torque, whereas the axial alignment enables faster turning in or out and more precise angular guidance in many applications.

According to one embodiment, the handle is in the form of a ratchet handle.

It is in particular contemplated that such a ratchet handle comprises a plastic gear which is accommodated in the main body and into which a pawl engages, which blocks the rotation of the plastic gear in one direction of rotation.

In this way, a simply configured ratchet mechanism can be provided, which consists of only a few parts.

In particular, the ratchet mechanism is preferably not designed to be switchable. In order to change the direction of rotation, the tool can be locked into the receptacle from two different sides.

The gear is in particular an integral part of the tool receptacle.

In particular, the gear forms part of a sleeve which comprises at least one, preferably two resilient hooks that can be used to lock the tool, in particular the screwdriver.

The set may furthermore comprise at least one tool selected from the group consisting of a guide sleeve that can be fitted onto a bone screw, a dilator, a counter holder for a guide sleeve, a holder for a fusion rod, and a flank breaker for the tulip on a fusion screw.

The holder for the fusion rod can preferably be coupled to the handle. In this way, a particularly compact holder can be provided.

According to one embodiment, the flank breaker for the tulip of the fusion screw comprises the counter holder for the guide sleeve.

In particular, the flank breaker may have one end with a drive, for example a hexagon, and a further end having a channel into which the flank can be introduced and can then be broken off.

In this way, a tool with double functionality is provided, which reduces the number of required tools and permits the set to be provided more cost-efficiently.

The disclosure also relates to the flank breaker as described above, regardless of whether it forms part of the set described above.

Furthermore, the disclosure relates to a handle for a medical tool, which is in particular designed for the set as described above.

The handle, i.e. at least the main body of the handle is made of plastics material, and the handle comprises a ratchet mechanism including a plastic gear in which a pawl engages, which blocks rotation in one direction of rotation.

The gear in turn forms part of a tool receptacle in which the drive of a tool, in particular of a screwdriver, can be locked.

The gear in particular forms part of a sleeve which comprises the tool receptacle.

As described above, the sleeve furthermore preferably comprises at least one resilient hook for locking the tool.

In particular, the resilient hook is an integral part of the sleeve. The hook may in particular be provided together with the sleeve as an integral, i.e. one-piece injection-molded component.

In a refinement, the set for dorsal spinal fusion furthermore comprises a needle, in particular an access needle.

An access needle comprises a hollow needle which can be separated from an inner needle.

Such a medical instrument is also referred to as a trocar. The trocar is an instrument which is used in minimally invasive surgery, i.e. laparoscopic surgery, to create access to a body cavity, by a sharpened or non-bladed tip, and to hold it open by the hollow needle, also referred to as a hollow tube. The inner needle is an awl accommodated in the hollow tube and having a tip that closes the opening of the tube.

Once the trocar has been inserted, the inner needle is retracted, i.e. it can be separated from the trocar.

The needle, in particular the hollow needle, has a groove for engagement of the resilient hook therein.

In particular, the set comprises a further handle for the needle.

This handle may have a different ergonomic design than the handle described above.

The handle is used to position the access needle.

In a refinement, the handle comprises a coupling for an extension, in particular an angled extension.

The extension allows the access needle to be positioned under X-ray control without requiring the user to reach into the beam path.

In particular the counter holder/flank breaker described above can be used as an extension.

The coupling may in particular be provided in the form of a hexagon on the proximal side of the handle.

The disclosure moreover relates to a handle which in particular has one or more of the features described above.

The handle is made of plastics material and comprises a tool receptacle in which the drive of a second tool can be locked.

The locking is effected by a hook which is an integral part of the handle, in particular of a main body of the handle.

As described above, in particular the main body of the handle or a component of the handle such as the sleeve of the ratchet mechanism described above may come in the form of a one-piece, i.e. integral injection-molded component including the resilient hook.

The disclosure furthermore relates to a handle which in particular has one or more of the features described above.

The handle has a long side and a narrow end, and a respective receptacle in which a tool can be locked is provided on both the long side and the narrow end.

Thus, the handle can be used in different ways, depending on the user's preference.

More particularly, the handle is designed so that it can be coupled to the tool in two orientations rotated by 90°.

In axial alignment with the tool, the handle can even be used as a mere extension of a tool, in particular of the set for dorsal spinal fusion, and not as a drive for turning.

According to one embodiment, the receptacle on the long side comprises a ratchet mechanism.

According to a further embodiment, the handle is configured for being coupled with a needle, in particular an access needle.

For this purpose, the handle may have a passage for the needle.

A needle coupled to the handle has a groove in which the resilient hook of the handle engages.

In particular a hollow needle will have the groove. Thus, the hollow needle can be snap-connected to the handle and detached from the handle.

An inner needle can preferably be retracted out of the handle and the hollow needle coupled to the handle on the proximal end.

The inner needle may comprise a holder which in turn can be coupled to the handle, in particular by a thread inside the passage for the needle.

In a refinement, the handle has a coupling for an extension on a proximal end thereof, in particular for an angled extension such as for the counter holder described above, for example.

The handle for the needle is preferably designed with a shape such that it can be gripped laterally with respect to the needle. For this purpose, the handle may have a cylindrical or bulbous shape.

The disclosure also relates to a needle which is coupled to a handle as described above and is in particular in the form of an access needle.

BRIEF DESCRIPTION OF THE DRAWINGS

The invention will now be explained in more detail with reference to an exemplary embodiment shown in the drawings of FIGS. 1 through 18.

FIG. 10 is a perspective view of the sleeve including a gear which is part of the ratchet mechanism.

FIG. 11 is a perspective sectional view of the sleeve.

FIG. 12 shows a perspective view of the sleeve together with the pawl.

DETAILED DESCRIPTION

Figure 1:
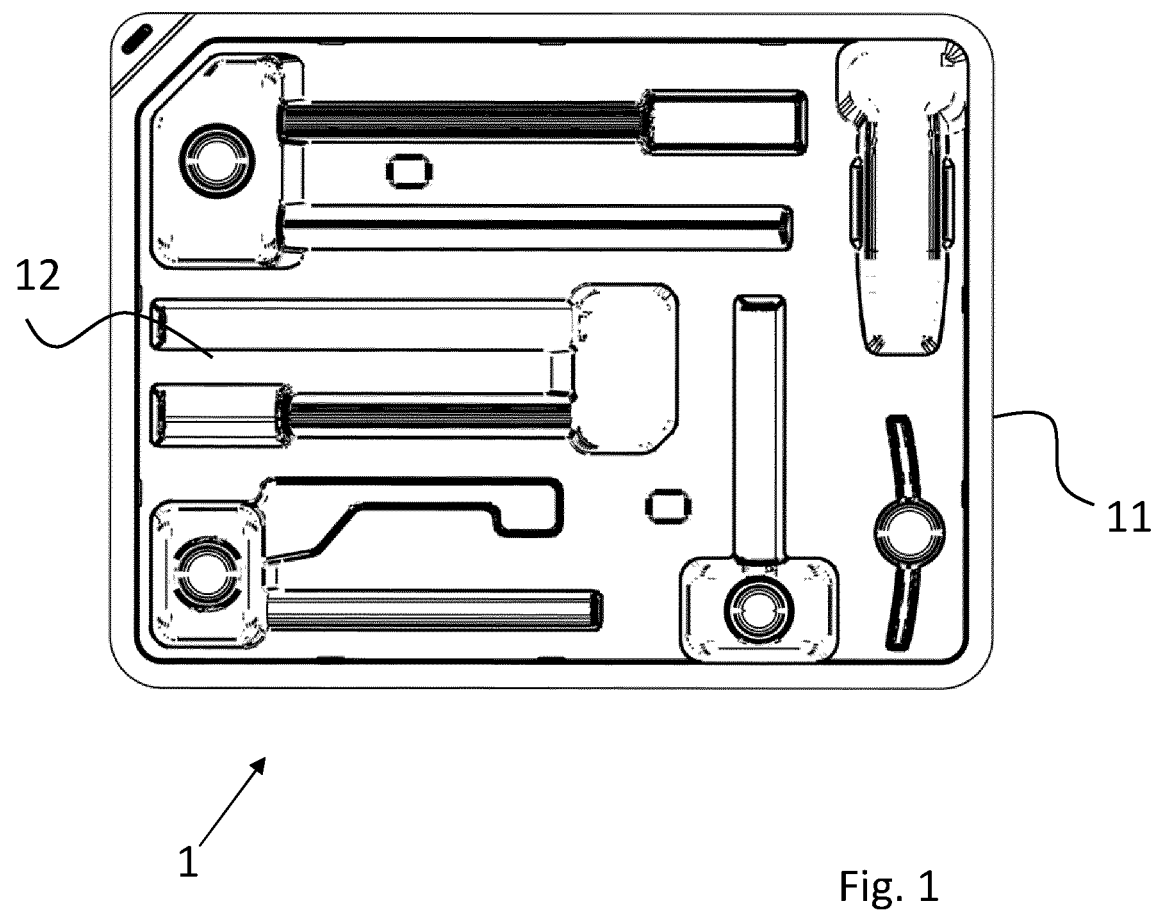
FIG. 1 shows a top plan view of a set for dorsal spinal fusion.

FIG. 1 is a top plan view of a set 1 for dorsal spinal fusion, which comprises at least some of the instruments used for this purpose.

The set comes in the form of a blister pack 11 which comprises a tear-off transparent film 12.

Figure 2:
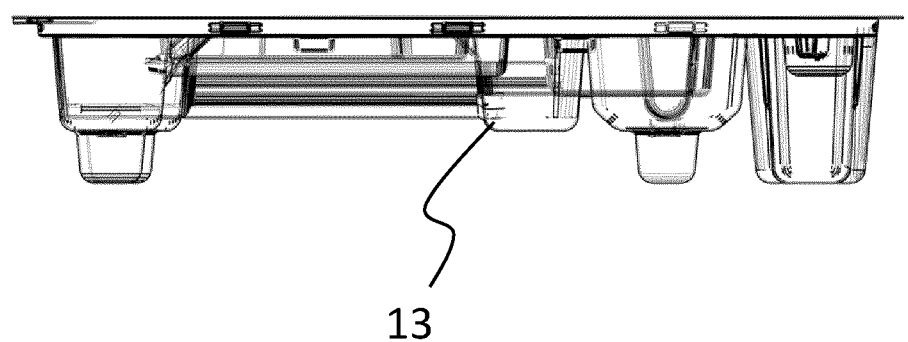
FIG. 2 shows the set in a side view of the long side.

As can be seen in the side view of FIG. 2, the blister pack comprises a molded tray 13 which has depressions for the individual instruments.

This allows, in a simple manner, to provide a clear arrangement with a defined position of the individual instruments.

Figures 3, 4:
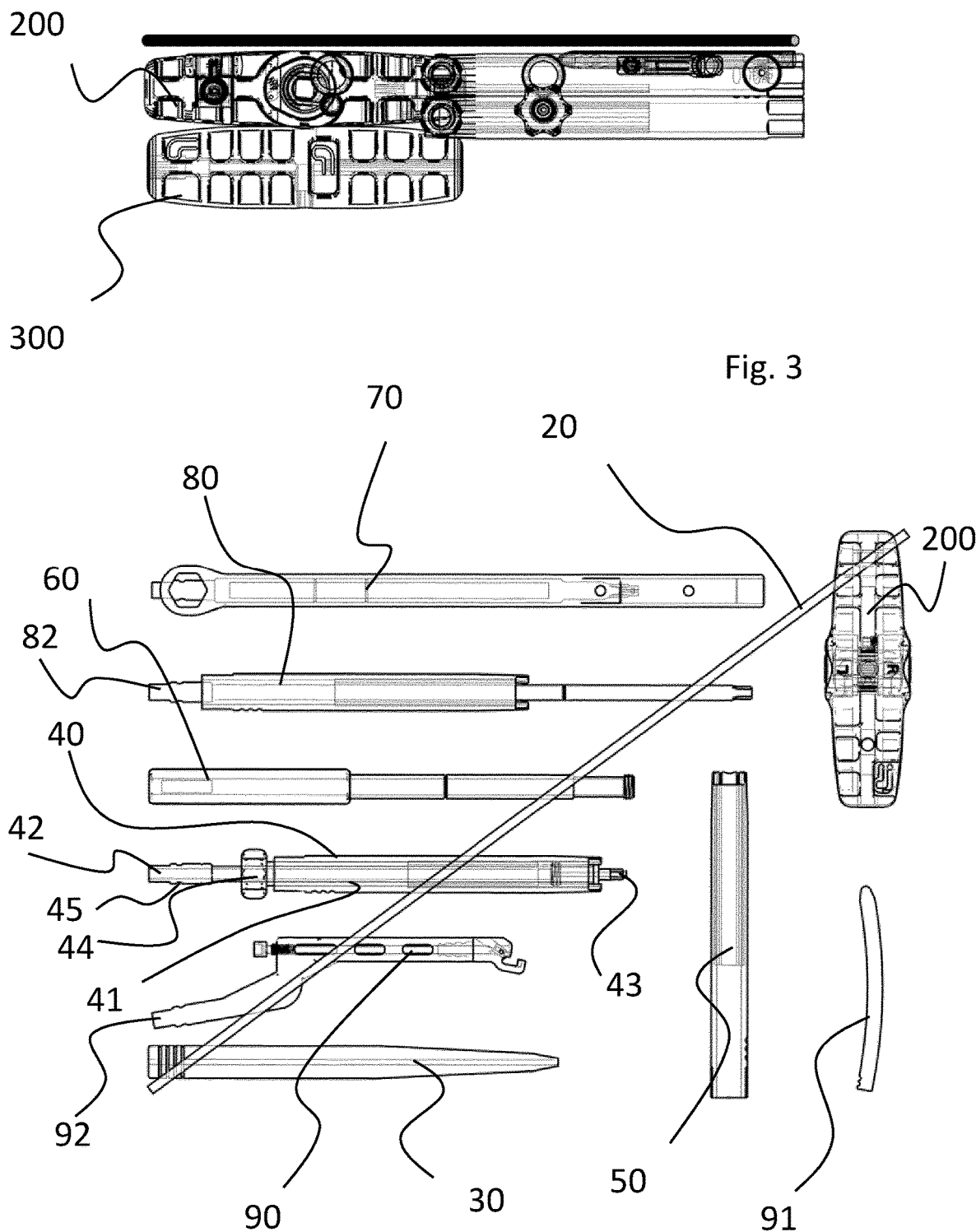
FIG. 3 shows the set in a side view of the narrow side.
FIG. 4 shows the instruments included in the set, by way of example.

FIG. 3 is a side view of the narrow side of the set.

As can be seen, two handles are arranged one above the other in one of the troughs of the molded tray, namely a handle comprising a ratchet mechanism 200 and a further handle 300 without a ratchet mechanism.

Depending on which instrument is coupled at the respective moment and depending on the preference of the user, one of the two handles 200 or 300 can be used.

FIG. 4 shows the instruments provided in the set, in a top view.

In this exemplary embodiment, in addition to the handle 200, the set includes a guide wire 20 which is introduced through an access needle. In the present exemplary embodiment, the access needle is not part of the set, since most surgeons have a particular preference for a specific access needle.

The set furthermore comprises a dilator 30 which can be fitted onto the guide wire 20 and can be used to expand the soft tissue.

For introducing the fusion screws, the set comprises the screwdriver 40. Screwdriver 40 comprises a sleeve 41 with a handle 44, and mounted therein for rotation is a drive 42 which is coupled to the screw drive 43 and is intended to be fastened to the handle 200.

The drive 42 in particular has a polygonal shape, for example a square shape, in order to be driven in a positive or form-fitting manner by the correspondingly shaped receptacle of the handle.

A groove 45 is provided adjacent to the drive 42, for engagement of a locking means therein for axially securing the screwdriver, in the present set a resilient hook of the handle 200.

For using the screwdriver 40, the drive 42 thereof is introduced into the handle 200.

The screwdriver 40 can be introduced and removed without using tools.

The set moreover comprises guide sleeves 50 which can be coupled to the fusion screws and which can in particular be used to align the fusion screws.

The position or orientation of the fusion screws can be altered using a distraction tool 60 which can be introduced into the tulip of the screw.

The screwdriver 80 is used to introduce a lock which is used to connect the fusion rod to the screw. The screwdriver 80 can also be coupled to the handle 200, via a drive 82.

The set furthermore comprises a combined counter-holder/flank breaker 70 which on the one hand can be used to hold in position the guide sleeves 50, and which on the other hand can be used to break off the flanks of the tulip of the fusion screw at the end of the surgery.

The rod 91 included in the set can be coupled to the rod holder 90, but is only used to verify whether the fusion screws are correctly aligned.

Then, the fusion rods are introduced using the rod holder 90.

The rod holder 90 also comprises a drive 92 and can thus be coupled to the handle 200.

Figure 5:
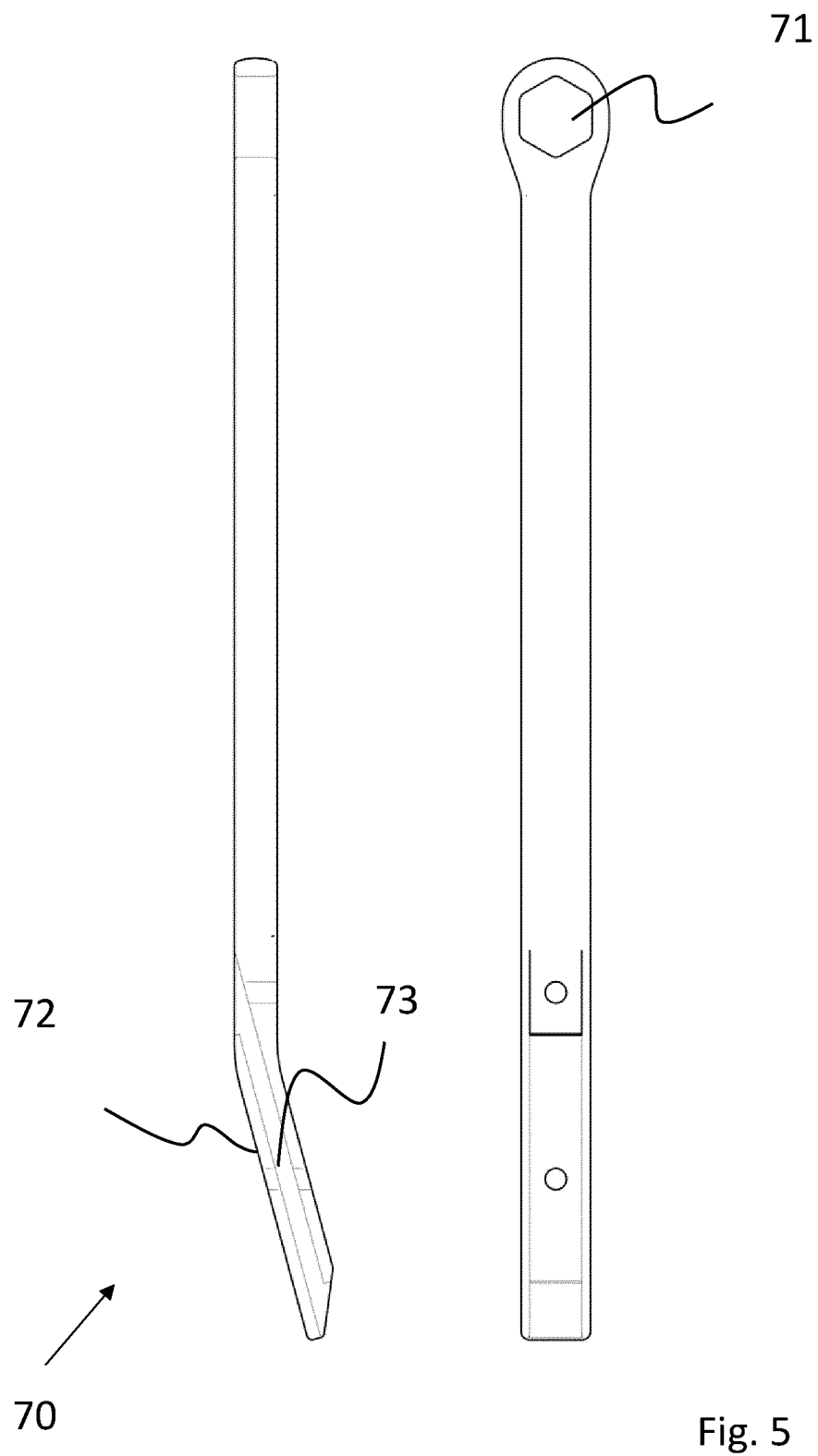
FIG. 5 is a view of the flank breaker included in the set.

FIG. 5 is a view of the combined counter holder/flank breaker.

It comprises a wrench 71 on one end, in particular in the form of a hexagon. This can be used as a counter holder for the guide sleeves 50 shown in FIG. 4.

On its opposite end, the combined counter holder/flank breaker 70 has an angled head portion 72 including a channel 73.

The channel 73 can serve to fit the tool on the flank of the fusion screw and then the flank can be broken off The combined counter-holder/flank breaker is preferably made of plastics material, in particular in the form of an integral injection-molded plastic component.

Figure 6:
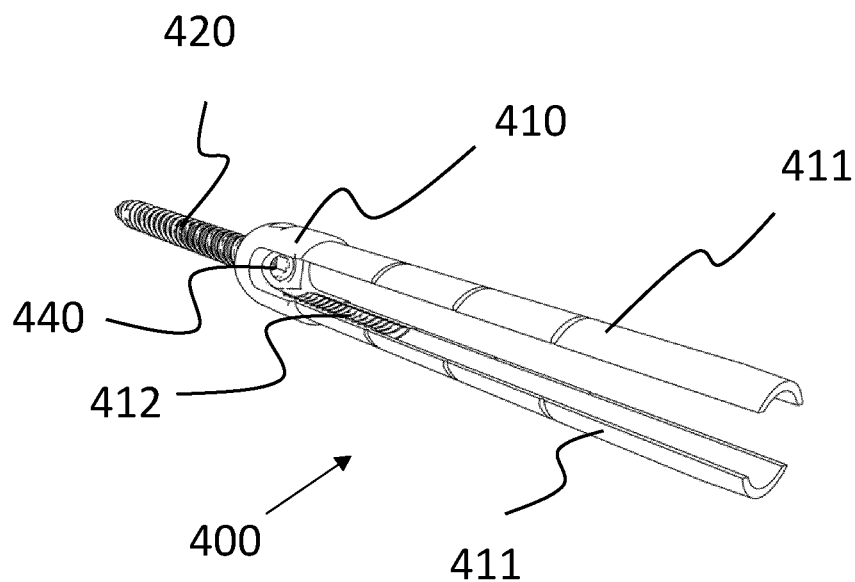
FIGS. 6 and 7 are perspective views of a screw which can be introduced using the instruments of the set.
Figure 7:
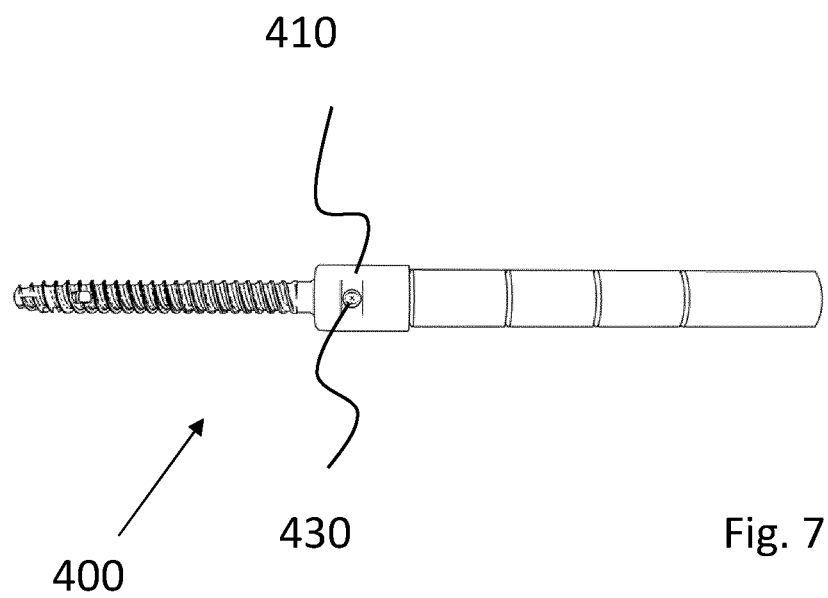

FIGS. 6 and 7 are perspective views of a screw 400 which can be processed using the instruments of the set according to the disclosure.

Screw 400 comprises a tulip 410 with flanks 411.

The flanks 411 may be segmented. For example, sections of the flanks 411 can be broken off in order to adapt the length of the flanks 411.

Furthermore, the tulip 410 has a thread 412 into which the distraction tools (reference numeral 60) as shown in FIG. 4 can be introduced.

The drive 440 of the screw 400, through which the thread 420 can be screwed into the bone, is provided inside the tulip 410.

The drive 440 may be in the form of a hexagon or a hexalobular socket, for example.

The screwdriver with reference numeral 40 as shown in FIG. 4 is used to introduce the screw 400 into the bone.

As can be seen in the view of FIG. 7, the tulip 410 has through holes 430 into which the rods can be introduced for fusion.

The rod for fusion of the vertebral bodies is fixed by a lock, not illustrated here, which can be screwed into the tulip 410 using the screwdriver with reference numeral 80 shown in FIG. 4.

Subsequently, the flanks 411 will be broken off using the flank breaker shown in FIG. 5.

Figure 8:
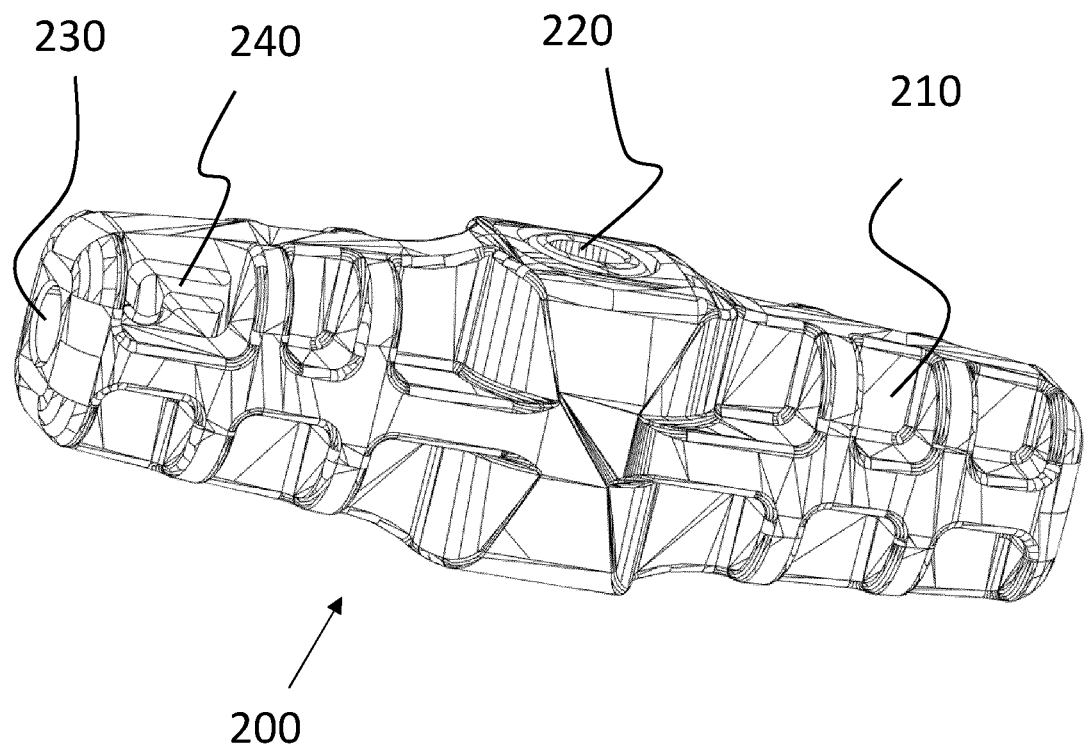
FIG. 8 is a perspective view of a ratchet handle.

FIG. 8 is a perspective view of a handle 200 which comprises a ratchet mechanism.

The handle 200 has an elongated shape and, in this exemplary embodiment, has an outer contour 210 suited to be grasped more easily.

A receptacle 220 for a tool, in particular for a screwdriver, is provided midway in the handle 200. The tool can be introduced into the receptacle 220 from both sides.

Moreover, the handle 200 has a further receptacle 230 on its narrow end, which serves to introduce a tool.

In this view, a resilient hook 240 can be seen, which serves to lock the tool which has a corresponding groove.

That means, the tool can be introduced and removed without the use of tools.

Figure 9:
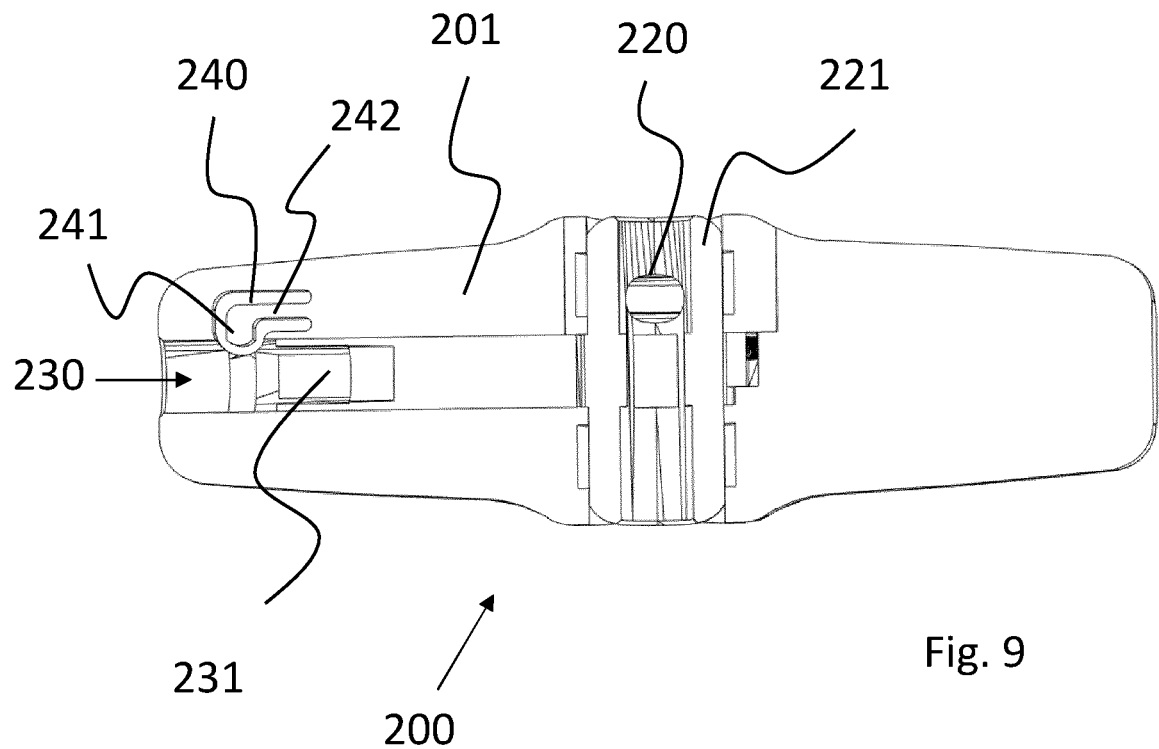
FIG. 9 is a sectional view of the ratchet handle.

FIG. 9 is a sectional view of the handle shown in FIG. 8.

The tool receptacle 230 can be seen, which has a polygonal, in particular square portion 231 for driving the tool. Adjacent to the polygonal portion 231, the resilient hook 240 protrudes into the tool receptacle 230.

The polygonal portion 431 is made of the same plastics material as the rest of the handle. In this way, a complex insert made of metal can be dispensed with.

The resilient hook 240 comprises an engagement member 241 which is rounded at its end in this exemplary embodiment, and which engages in a groove of the tool that is used.

When the tool is introduced and removed, the resilient hook 240 will bend sideways. In the introduced state, the resilient hook 240 engages in a groove in the tool (45 in FIG. 4).

When the tool is introduced or removed, the engagement member 241 is able to snap in by virtue of an angled resilient beam 242 that is formed integrally with the main body 201 of the handle.

The resilient hook 240 is made of plastics material and is formed integrally with the handle 200.

Depending on preference, the user can either use the receptacle 230 to assemble the handle 200 axially relative to the tool, in accordance with its main extension direction, or can use the receptacle 220 to couple the tool to the handle in a T-shaped assembly.

Handle 200 includes a ratchet mechanism which comprises a sleeve 221 including the receptacle 220.

FIG. 10 is a perspective view of this sleeve 221.

Sleeve 221 is made of plastics material and comprises a gear 222 as an integral component thereof.

Gear 222 is provided at a midway position of the sleeve 221.

Above and below the gear 222, there are two portions extending, each one with a resilient hook 240 provided thereon, as can be seen in the perspective sectional view of FIG. 11.

The resilient hook 240 is formed similar to the resilient hook illustrated in FIG. 9.

Resilient hook 240 may in particular be L-shaped.

The resilient hooks 240 which form an integral part of the sleeve 221 that is made of plastics material allow a tool to be introduced from both sides and to be locked by the resilient hooks 240.

Centrally, the sleeve 221 has a polygonal portion 243 which serves to drive the tool.

The polygonal portion 243 is provided inside the gear 222.

FIG. 12 is a perspective view of the sleeve 221 and of a pawl 223 which is biased against the gear 222 of the sleeve by a spring 226.

Pawl 223 is attached to the main body.

The pawl 223 engages in the gear 222 and thus has the effect that the sleeve 221 can only be rotated in one direction relative to the main body.

In one direction of rotation, counterclockwise in this view, the pawl 223 is able to yield against the bias of the spring 226 so as to allow the sleeve 221 to rotate.

In the other direction, the teeth of the gear 222 will abut against the pawl 223, so that rotation is blocked.

For switching the desired direction of rotation, the tool can be introduced into the sleeve 221 from both sides.

Figure 13:
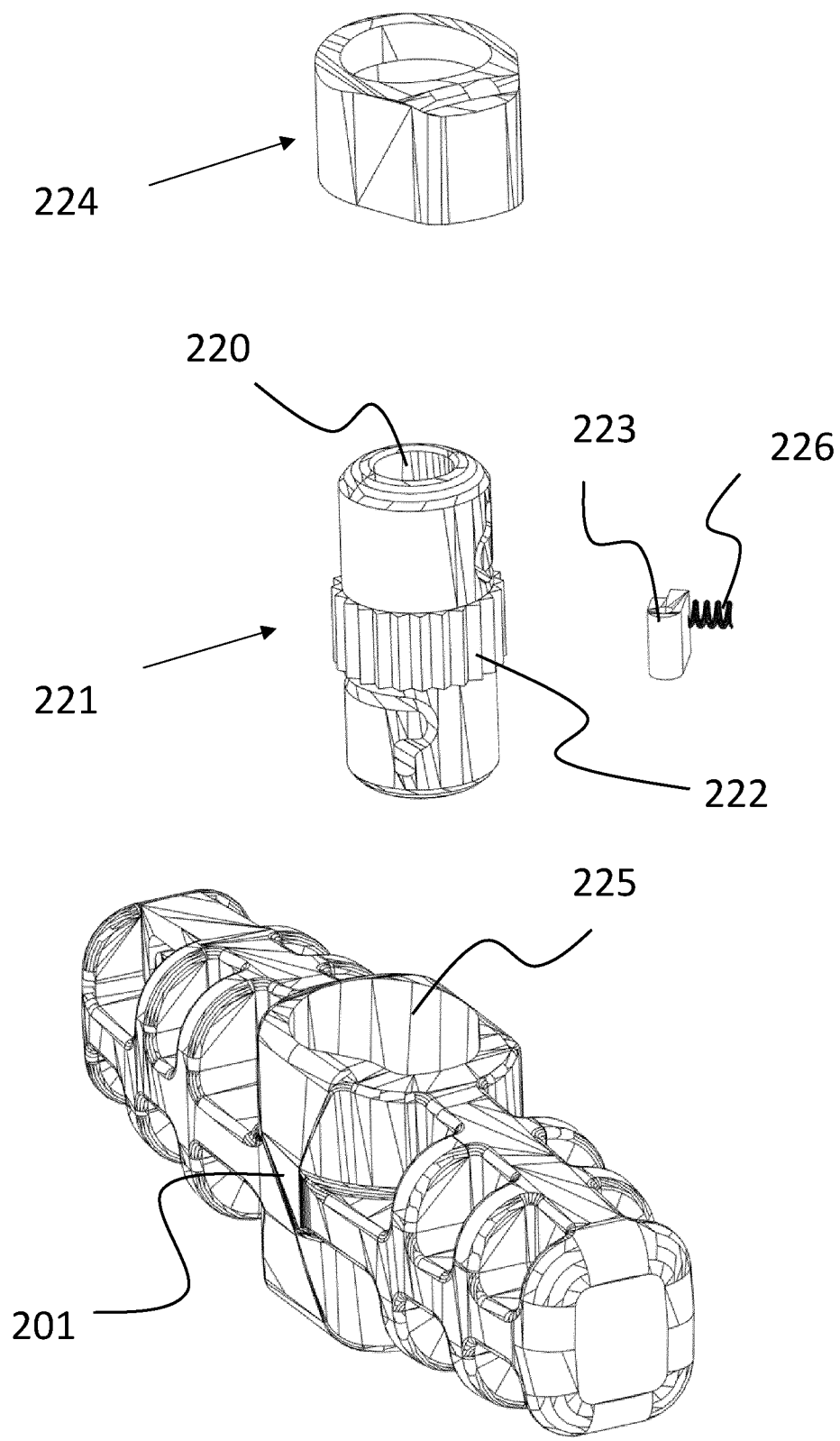
FIG. 13 is an exploded perspective view of the components of the handle.

FIG. 13 shows an exploded view of the components of the handle with the ratchet mechanism.

The handle consists of a main body 201 which has a recess 225 for accommodating the ratchet mechanism.

Sleeve 221 is introduced into the recess 225 and is mounted for rotation there.

During assembly of the handle, the pawl 223 with spring 226 is introduced prior to introducing the sleeve comprising the receptacle 220 and the gear 222.

Then, the sleeve 221 together with the pawl 223 and spring 226 is axially secured by introducing the insert 224 into the recess 225.

Insert 224 can be snap-fitted or can be fixed by a material bond e.g. by gluing or welding.

In this way, the components of the ratchet mechanism are secured in a simple manner in the recess 225 of main body 201.

With the exception of the pawl 223 and the spring 226, all other components of the handle are preferably made of a plastics material. In particular, they come in the form of injection molded components.

Figure 14:
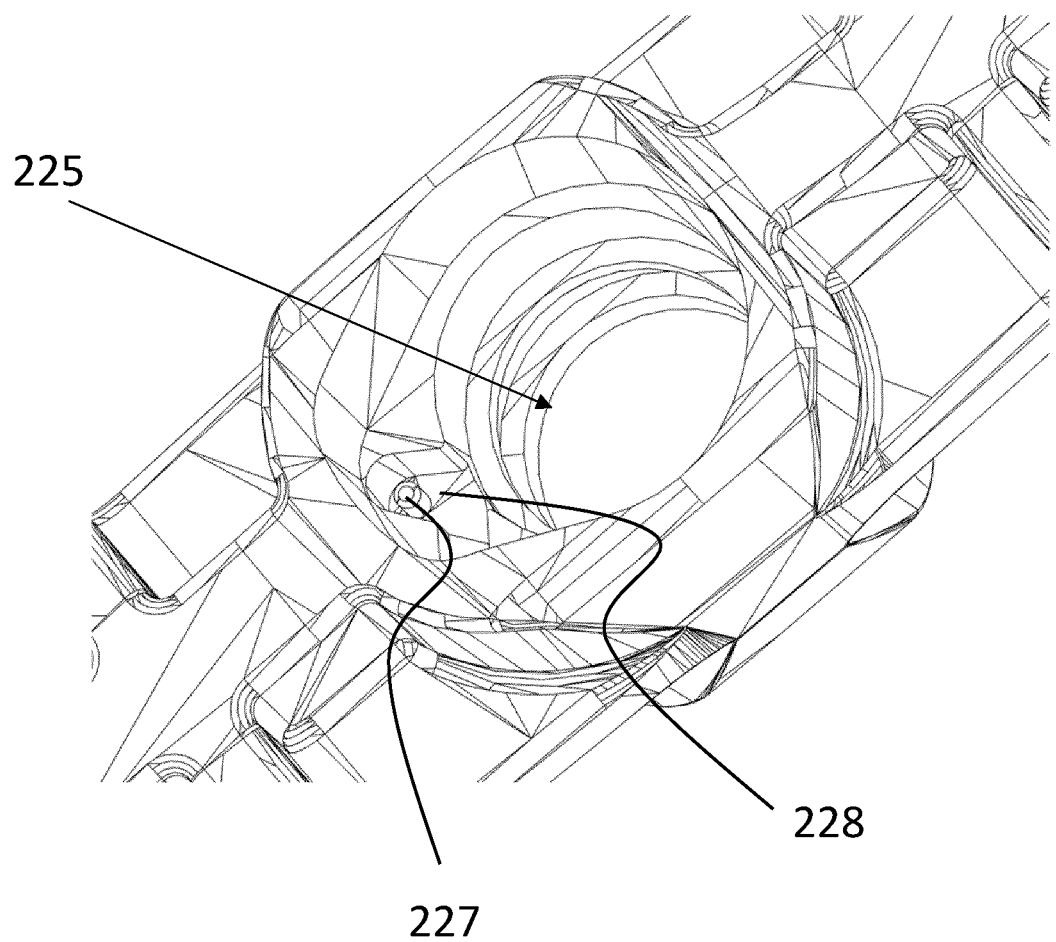
FIG. 14 is a perspective view of a detail, showing the recess in which the ratchet mechanism is arranged.

FIG. 14 is a detailed perspective view of the recess 225.

As can be seen inside the recess 225, the main body has a recess 228 for the pawl together with the spring.

A shaft 227 for the pawl is formed as an integral pin-shaped portion of the main body.

The pawl is introduced into the recess 228 together with the spring.

Then, the sleeve 221 is placed in the recess 225, and the assembly is completed by introducing the insert 224.

Figure 15:
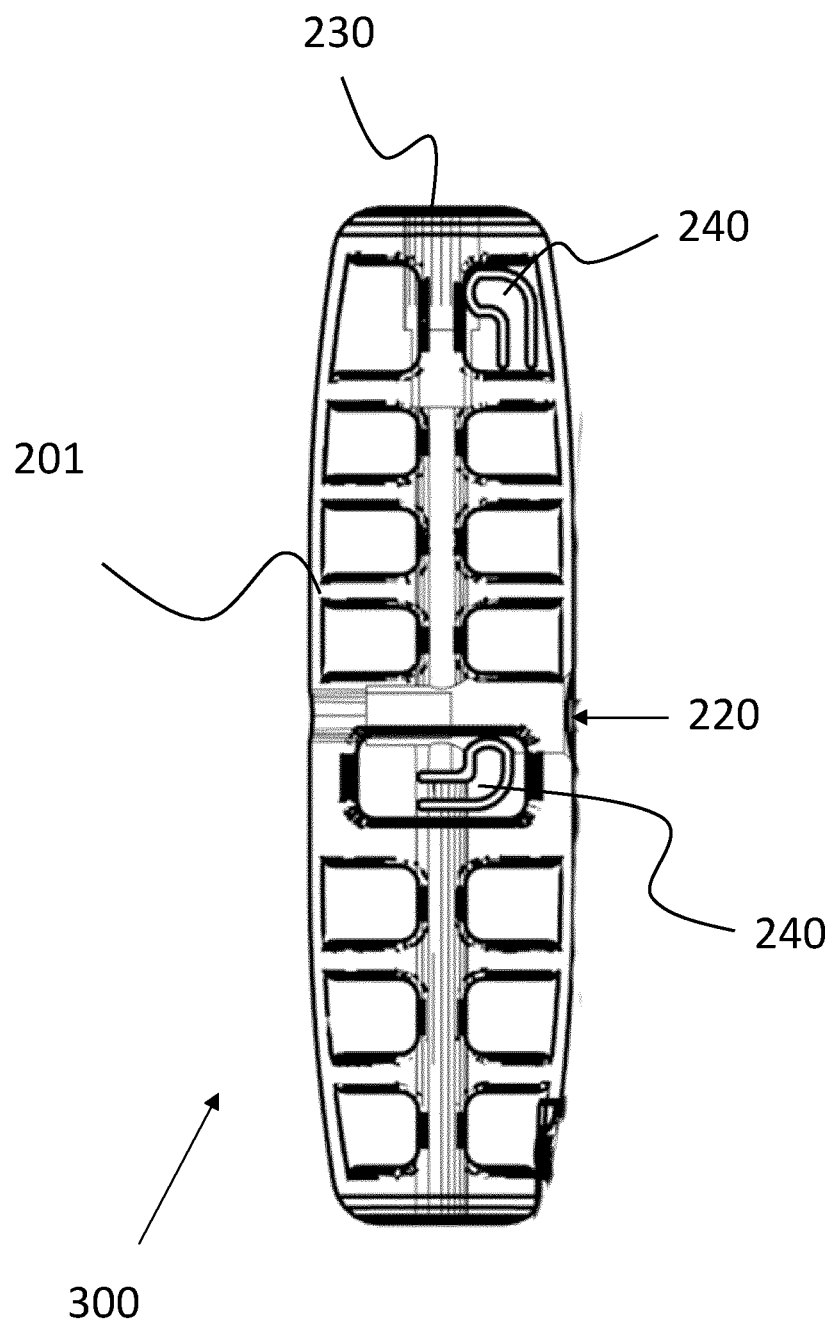
FIG. 15 is a view of another handle which does not have a ratchet mechanism.

FIG. 15 shows a side view of a handle 300 that does not comprise a ratchet mechanism.

This handle can also be coupled to the tool in a T-shaped configuration as well as axially aligned.

For this purpose, the handle 300 comprises the receptacle 220 into which the tool, such as the screwdriver, can be introduced.

A resilient hook 240 which is an integral part of the main body 201 of the handle allows to lock the handle in place without the use of tools.

Furthermore, the handle 300 has a receptacle 230 for a tool on its narrow end, similar to the handle with reference numeral 200 illustrated before.

Again, in this receptacle, the inserted tool is also locked by a resilient hook 240 which engages laterally in a groove.

At least one of the resilient hooks may be formed so as to open to one side, as illustrated here.

On the one hand, this ensures easy removability from the mold during injection molding.

On the other hand, a visual check is made possible in this way as to whether the resilient hook 240 is actually engaged in the groove of the tool.

Figure 16:
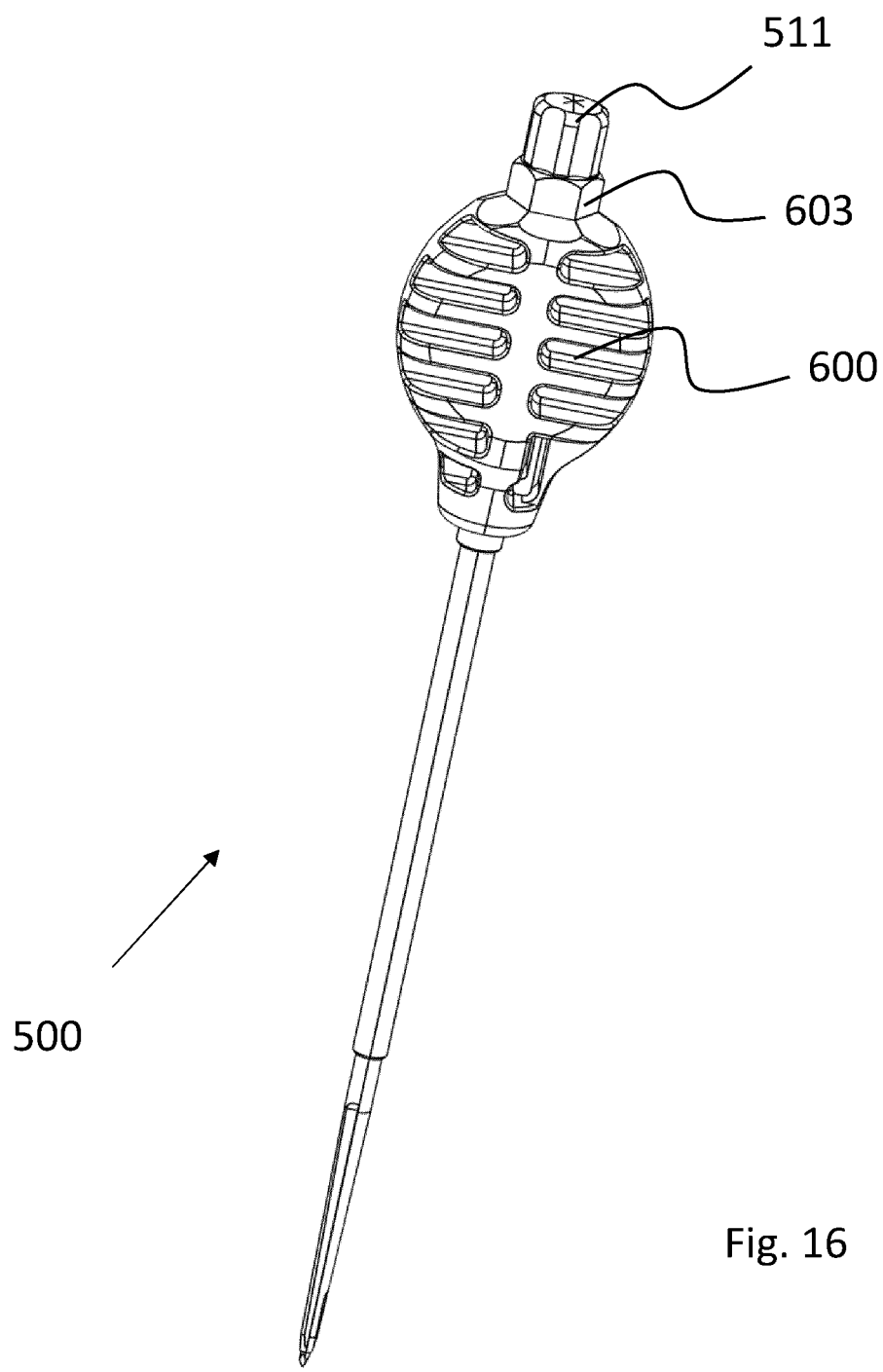
FIG. 16 is a view of one exemplary embodiment of a handle comprising an access needle.

FIG. 16 is a view of one embodiment of an access needle 500 with a handle 600.

Handle 600 is designed for being gripped from the side. Proximally, the handle 600 comprises a coupling 603 for a holder (see e.g. FIG. 4). In this way, it is possible for the handle 600 to also be guided under X-ray control from outside the beam path. The coupling 603 may, for example, be in the form of a polygon, e.g. a hexagon.

An inner needle 510 can be retracted via a proximal holder 511.

Figure 17:
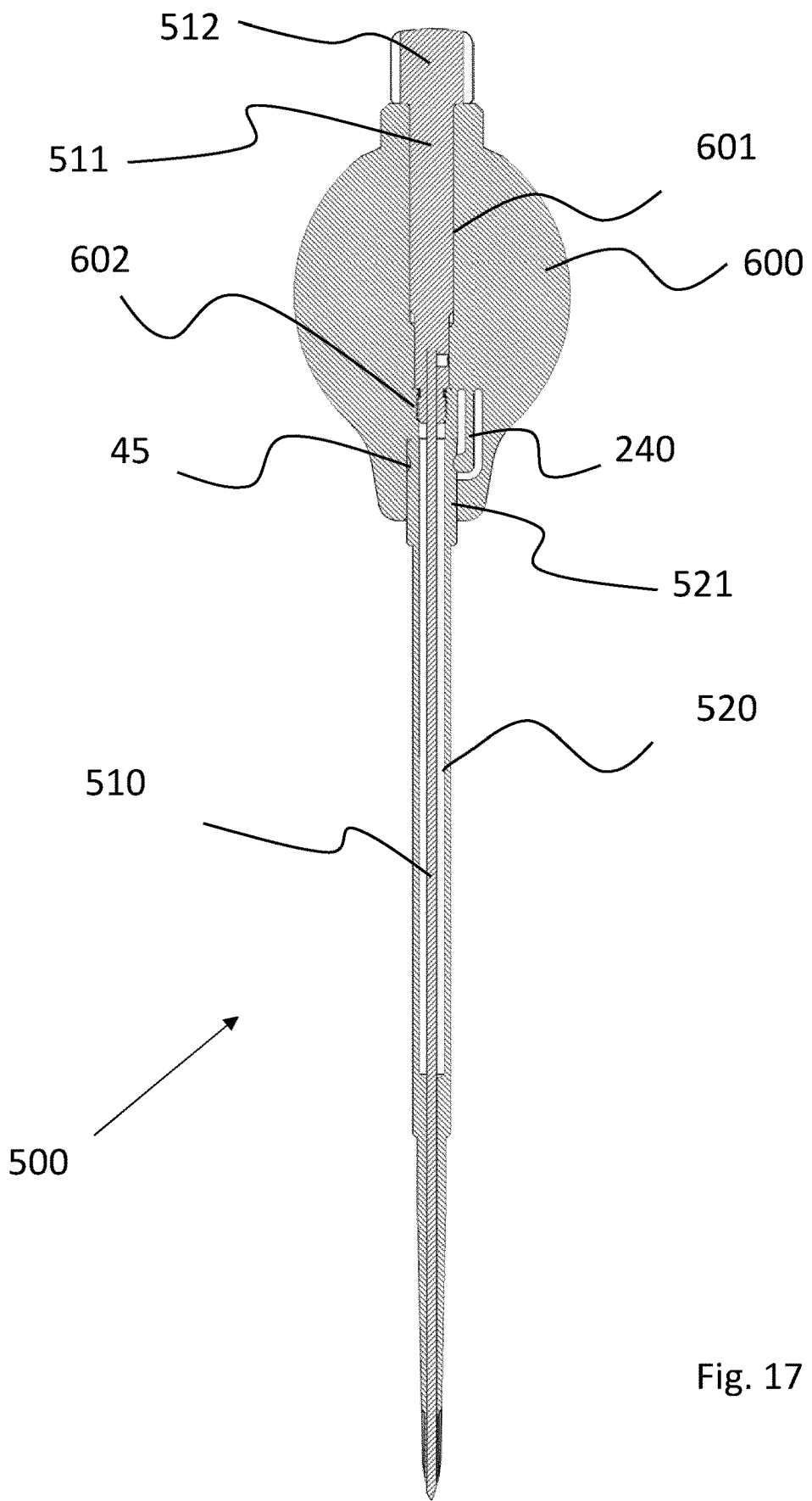
FIG. 17 is a sectional view of the handle with the needle of FIG. 16.

FIG. 17 is a sectional view of the access needle 500 which comprises a hollow needle 520 with an inner needle 510.

Handle 600 has a passage 601 for the needles 510, 520.

The hollow needle 520 is latched near the distal end of the handle 600. An insert 521 which is preferably secured against rotation relative to the handle 600 has a groove 45 in which a resilient hook 240 of the handle 600 engages.

The resilient hook 240 is an integral pa of the handle 600 made of plastics material and may in particular be designed in accordance with the exemplary embodiments as described above. Hook 240 is in particular openly accessible from one side.

Proximally of the hollow needle 520, the holder 511 of the inner needle 510 extends through the passage 601. Holder 511 is joined to the handle 600 by a thread 602 inside the passage 601.

Proximal head piece 512 serves to unscrew the holder 511 together with the inner needle 510 and to remove the inner needle 510 in this way.

The outer needle 520, in turn, can be pulled out from the distal end by releasing the latched connection.

Figure 18:
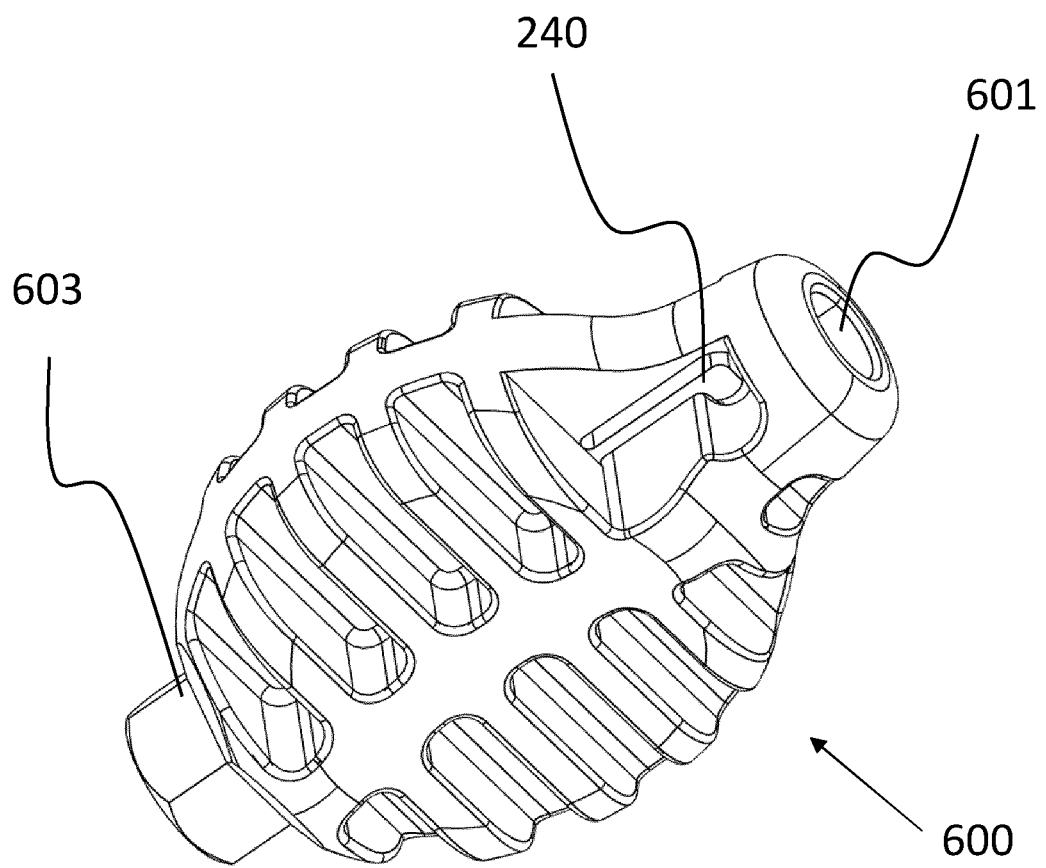
FIG. 18 shows the handle in a detailed view.

FIG. 18 is a perspective view of the handle 600 alone. Handle 600 is in the form of a monolithic body made of a fiber-reinforced plastic, including the hook 240 and the coupling 603.

The disclosure made it possible to provide a single-use set of instruments for dorsal spinal fusion which is inexpensive to manufacture and provides for good handling and flexibility.

The articles "a" and "an" as used in this application and the appended claims should generally be construed to mean "one or more" unless specified otherwise or clear from context to be directed to a singular form.

LIST OF REFERENCE NUMERALS

1 Set for dorsal spinal fusion
11 Blister pack
12 Transparent film
13 Molded tray
20 Guide wire
30 Dilator
40 Screwdriver
41 Sleeve
42 Drive
43 Screw drive
44 Handle
45 Groove
50 Guide sleeve
60 Distraction tool
70 Combined counter holder/flank breaker
71 Wrench
72 Head of flank breaker
73 Channel
80 Screwdriver (for lock)
90 Rod holder (for fusion rod)
91 Rod
92 Drive
200 Handle
201 Main body
210 Outer contour
220 Receptacle
221 Sleeve
222 Gear
223 Pawl
224 Insert
225 Recess
226 Spring
227 Shaft
228 Recess
230 Receptacle
231 Polygonal portion
240 Hook
241 Engagement member
242 Resilient beam
243 Polygonal portion
300 Handle
400 Screw
410 Tulip
411 Flank
412 Thread
420 Thread
430 Through hole
440 Drive
500 Access needle
510 Inner needle
511 Holder
512 Head piece
520 Hollow needle
521 Insert
600 Handle
601 Passage
602 Thread
603 Coupling

The invention claimed is:

1. A set for dorsal spinal fusion (1), comprising:
a detachable handle (200) made of plastic material and
a screwdriver (40) that can be coupled to the detachable handle (200) without the use of tools,
wherein the detachable handle (200) has a receptacle (220) for the screwdriver (40), the receptacle (220) being made of plastic material,
wherein the detachable handle (200) includes a ratchet mechanism,
wherein the ratchet mechanism comprises a sleeve (221),
wherein the sleeve (221) includes the receptacle (220),
wherein the sleeve (221) is made of plastic material and comprises a plastic gear (222) as an integral component thereof, wherein the sleeve (221) comprises two portions, one of the two portions extending above the gear (222) and another of the two portions extending below the gear (222), wherein each of the two portions includes a resilient hooks (240) as an integral part of the sleeve (221), and wherein the resilient hooks (240) are configured to engage a groove of the screwdriver (40).

2. The set for dorsal spinal fusion (1) as in claim 1,
wherein the detachable handle (200) is made of polyacrylamide.

3. The set for dorsal spinal fusion (1) as in claim 1,
wherein the ratchet mechanism includes a pawl (223) that engages the plastic gear (222) and thereby block rotation of the plastic gear (222) in one direction of rotation.

4. The set for dorsal spinal fusion (1) as in claim 1,
further comprising a guide sleeve (50) that can be fitted onto a bone screw, a dilator (30), a counter holder (70) for a guide sleeve, a holder for a fusion rod, and/or a flank breaker (70) for the tulip of a fusion screw.

5. The set for dorsal spinal fusion (1) as in claim 4,
wherein the flank breaker (70) for the tulip of the fusion screw comprises the counter holder (70) for the guide sleeve (50).

6. The set for dorsal spinal fusion (1) as in claim 1,
wherein the set is a sterile single-use set comprising a tear-open packaging.

7. The set for dorsal spinal fusion (1) as in claim 1,
further comprising an access needle (500), wherein the access needle (500) has a groove for engagement of the resilient hook (240) of a further handle (600) for the access needle (500).

8. The set for dorsal spinal fusion (1) as in claim 1,
wherein the resilient hook (240) is L-shaped.

9. The set for dorsal spinal fusion (1) as in claim 1,
wherein the screwdriver (40) is inserted into the receptacle (220) of the sleeve (221) from both sides according to the desired direction of rotation.

10. The set for dorsal spinal fusion (1) as in claim 1,
wherein the detachable handle (200) has a further receptacle (230) on its narrow end.

11. The set for dorsal spinal fusion (1) as in claim 1,
wherein the gear (222) is positioned midway of the sleeve (221).

12. A handle (200) made of plastic material comprising a receptacle (220) for a screwdriver (40), the receptacle (220) being made of plastic material
wherein the handle (200) includes a ratchet mechanism,
wherein the ratchet mechanism comprises a sleeve (221),
wherein the sleeve (221) includes the receptacle (220),
wherein the sleeve (221) is made of plastic material and comprises a gear (222) as an integral component thereof,
wherein the sleeve (221) comprises two portions, one of the two portions extending above the gear (222) and another of the two portions extending below the gear (222),
wherein each of the two portions includes resilient hooks (240) as an integral part of the sleeve (221), and
wherein the resilient hooks (240) are configured to engage a groove of the screwdriver (40).

13. The handle (200) as in claim 12,
wherein the handle (200) has a passage for an access needle (500).

14. The handle as in claim 12,
wherein the handle (200) is coupled to an access needle (500).

15. The handle (200) as in claim 14,
wherein the handle (200) has a coupling for an angled extension on a proximal end thereof.

16. The handle (200) as in claim 15,
wherein the ratchet mechanism includes a pawl (223) that engages the gear (222) and blocks rotation in one direction of rotation.

17. The handle as in claim 12,
wherein the receptacle (230) is used to couple the tool to the handle (200) axially.

18. The handle as in claim 12,
wherein the receptacle (220) is used to couple the tool to the handle (200) in a T-shape assembly.

* * * * *